(12) United States Patent
Cao et al.

(10) Patent No.: US 12,392,778 B2
(45) Date of Patent: Aug. 19, 2025

(54) METHOD FOR PROTEOME-WIDE DISCOVERY OF COVALENT LIGANDS AND COMPOSITIONS THEREOF

(71) Applicant: BridGene Biosciences, Inc., San Jose, CA (US)

(72) Inventors: Ping Cao, San Jose, CA (US); Yuan Yuan, San Jose, CA (US); Chao Zhang, San Jose, CA (US)

(73) Assignee: BridGene Biosciences, Inc., San Jose, CA (US)

( * ) Notice: Subject to any disclaimer, the term of this patent is extended or adjusted under 35 U.S.C. 154(b) by 733 days.

(21) Appl. No.: 17/630,815

(22) PCT Filed: Aug. 4, 2020

(86) PCT No.: PCT/US2020/044897
§ 371 (c)(1),
(2) Date: Jan. 27, 2022

(87) PCT Pub. No.: WO2021/026162
PCT Pub. Date: Feb. 11, 2021

(65) Prior Publication Data
US 2022/0276253 A1 Sep. 1, 2022

Related U.S. Application Data

(60) Provisional application No. 62/882,757, filed on Aug. 5, 2019.

(51) Int. Cl.
*G01N 33/58* (2006.01)
*G01N 33/68* (2006.01)

(52) U.S. Cl.
CPC ......... *G01N 33/58* (2013.01); *G01N 33/6848* (2013.01)

(58) Field of Classification Search
CPC ...... G01N 33/58; G01N 33/583; G01N 33/68; G01N 33/6803; G01N 33/6848; Y10T 436/17; Y10T 436/19; Y10T 436/200833; Y10T 436/24; Y10T 436/25375
USPC ... 436/86, 89, 106, 124, 128, 161, 164, 173, 436/177
See application file for complete search history.

(56) References Cited

U.S. PATENT DOCUMENTS

| 10,782,295 B2 * | 9/2020 | Cravatt | G01N 33/6842 |
| 2014/0193831 A1 | 7/2014 | Van Der Hoorn et al. | |
| 2017/0115303 A1 * | 4/2017 | Cravatt | G01N 33/5005 |

(Continued)

FOREIGN PATENT DOCUMENTS

| WO | WO-2017/070611 A1 | 4/2017 |
| WO | WO 2017/173035 A1 | 10/2017 |

OTHER PUBLICATIONS

Erdjument-Bromage et al., "Sample Preparation for Relative Quantitation of Proteins Using Tandem Mass Tags (TMT) and Mass Spectrometry (MS)," *Methods Mol. Biol.* (2018), 1741:135-149.

(Continued)

*Primary Examiner* — Maureen Wallenhorst
(74) *Attorney, Agent, or Firm* — Clark & Elbing LLP

(57) ABSTRACT

The present disclosure provides a profiling method based on comparative mass spectrometry analysis for identifying and quantifying the covalent interactions of electrophilic compounds with diverse proteins in complex proteomes, as well as compositions for performing the method.

11 Claims, 6 Drawing Sheets

(56) References Cited

U.S. PATENT DOCUMENTS

2019/0194709 A1    6/2019  Church et al.
2019/0346454 A1*  11/2019  Marto .................. C07C 233/33
2020/0048204 A1*   2/2020  Zhang ................. C07D 215/44
2020/0140388 A1*   5/2020  Woo ..................... C07D 401/04
2022/0214355 A1*   7/2022  Hsu ........................ A61P 29/00

OTHER PUBLICATIONS

Fischer et al., "Dasatinib, Imatinib and Staurosporine Capture Compounds—Complementary Tools for the Profiling of Kinases by Capture Compound Mass Spectrometry (CCMS)," *Journal of Proteomics* (2011), 75:160-168, Elsevier B.V.
Wall et al., "Detection of Electrophile-Sensitive Proteins," *Biochimica et Biophysica Acta* (2014), 1840:913-922. Blackwell Science Ltd.
Backus et al., "Proteome-wide covalent ligand discovery in native biological systems", Nature, Jun. 2016, 534(7608): 570-574.
EP Extended Search Report in European Application No. 20850895.2, dated Aug. 3, 2023, 10 pages.
Hoch et al., "Cysteine-reactive probes and their use in chemical proteomics", Chem. Comm., 2018, 54(36): 4501-4512.
Maurais et al., "Reactive-cysteine profiling for drug discovery", Curr. Opin. Chem Biol., Mar. 2019, 50(18): 29-36.
Roberts et al., "Chemoproteomic screening of covalent ligands reveals UBA5 as a novel pancreatic cancer target", ACS Chem. Biol., Feb. 2017. 12(4):899-904.
Ward et al., "NHS-esters as versatile reactivity-based probes for mapping proteome-wide ligandable hotspots", ACS Chem. Bio., Apr. 2017, 12(6): 1478-1483.

\* cited by examiner

METHOD FOR PROTEOME-WIDE DISCOVERY OF COVALENT LIGANDS AND COMPOSITIONS THEREOF

CROSS-REFERENCE TO RELATED APPLICATIONS

This application is a 35 USC § 371 National Stage application of International Application No. PCT/US2020/044897 filed Aug. 4, 2020, now; which claims the benefit under 35 USC § 119 (e) to U.S. Application Ser. No. 62/882,757 filed Aug. 5, 2019. The disclosure of each of the prior applications is considered part of and is incorporated by reference in the disclosure of this application.

BACKGROUND OF THE INVENTION

Field of the Invention

The invention relates generally to target discovery and more specifically to a profiling method based on comparative mass spectrometry analysis for identifying and quantifying the covalent interactions of electrophilic compounds with proteins in proteomes.

Background Information

Many drugs and drug candidates act by covalent modification of amino acid residues in particular proteins in cells. The predominant form of such covalent modification occurs between an electrophilic moiety in the drug or drug candidate and a nucleophilic amino acid in the protein. The discovery of additional chemical probes and drugs that can covalently modify particular proteins would benefit from a general method to globally map compound reactivity with various proteins in native biological systems.

There exists a need for improved methods for identifying and quantifying the binding interactions of reactive chemical probes with various components in whole cell proteomes.

SUMMARY OF THE INVENTION

The present invention provides a method and composition for ligand discovery by identifying and quantifying binding interactions of an electrophilic compound with as many as hundreds or thousands of proteins in parallel.

Accordingly, in one embodiment, the disclosure provides a method for identifying a protein target which covalently bind to a probe compound of interest. The method includes: a) contacting a proteomic sample (e.g., live cells, cell lysates, or live animals) with a probe compound having an electrophilic moiety and a clickable tag such as an alkyne moiety or azide moiety, wherein the electrophilic moiety covalently binds a nucleophilic amino acid residue in the protein target; and b) analyzing the proteomic sample to detect the proteins that are covalently bound by the probe compound, thereby identifying the protein target. In one aspect, the clickable tag is covalently linked to a detectable label and the nucleophilic amino acid residue is selected from arginine, lysine, histidine, cysteine, methionine, aspartic acid, glutamic acid, serine, threonine, tyrosine, tryptophan, and derivatives thereof. The clickable tag can be an alkyne group.

In another embodiment, the disclosure provides a method for identifying a protein target. The method include: (a) contacting a first protein-containing sample with a competitor compound harboring an electrophilic moiety and lacking a terminal clickable tag; (b) contacting the sample of (a) with a probe compound comprising the electrophilic moiety and the terminal clickable tag; (c) contacting a second protein-containing sample with the probe compound, wherein the electrophilic moiety binds a nucleophilic amino acid residue in the protein target; and d) identifying the protein target by detecting the amount of probe compound-modified proteins in the first protein-containing sample as compared to those in the second protein-containing sample. In one embodiment, the probe compound further includes a detectable label covalently derivatized off the clickable tag. In some embodiments, the detectable label can be biotin. The electrophilic reactive amino acid residue can be selected from arginine, lysine, histidine, cysteine, methionine, aspartic acid, glutamic acid, serine, threonine, tyrosine, tryptophan, and derivatives thereof. The clickable tag can be an alkyne group.

In some embodiments, the method further includes reacting the first protein-containing sample and the second protein-containing sample with a detectable label comprising a linker group reactive with the clickable tag in the probe compound. The method can also include enriching the detectable label-tagged protein target. In some embodiments, the method can further include preforming protease digestion of the enriched protein target. In some embodiments, the method can include quantifying and comparing the amount of various probe compound-bound proteins in the first protein-containing sample and the second protein-containing sample. The quantifying and comparing can be performed using liquid chromatography-mass spectrometry (LC-MS) with a tandem mass tag (TMT).

In various embodiments, the method further includes reacting the proteomic sample of a) and b) with a compound having a tag, for example biotin, to conjugate the biotin tag to protein targets. This compound will have a reactive group which can form covalent bond with the clickable tag of the probe molecules. When the tag is biotin, for example, the biotin-labeled protein targets may then be enriched by streptavidin and be subjected to protease digestion. The resulting peptides are then chemically labeled with isobaric mass tags to facilitate comparative mass spectrometry analysis.

In some embodiments, the electrophilic group on the probe compound can be selected from the group consisting of alkyl halide, haloacetyl, maleimide, aziridine, acryloyl halogen, maleimide, isothiocyanate, isocyanate, acyl azide, N-hydroxysuccinimide ester, sulfonyl chloride, epoxide, oxirane, carbonate, imidoester, carbodiimide, anhydride, diazoalkane, diazoacetyl, carbonydilmidazole, and carbodiimide. In some embodiments, the electrophilic group on a probe compound can be selected from the group consisting of

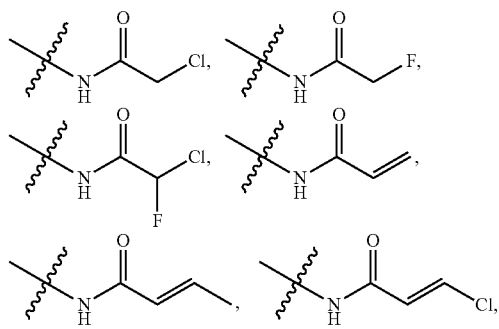

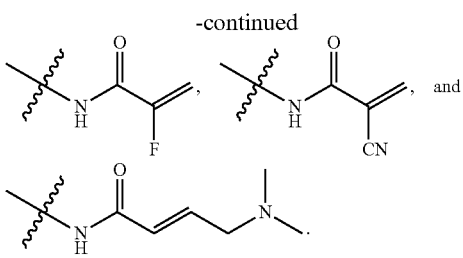

In yet another embodiment, the disclosure provides a modified non-naturally occurring protein that includes a nucleophilic amino acid residue covalently bound to a probe that includes a clickable tag covalently linked to a detectable label. In some embodiments, the detectable label can be biotin. In various embodiments, the electrophilic reactive amino acid residue is selected from arginine, lysine, histidine, cysteine, methionine, aspartic acid, glutamic acid, serine, threonine, tyrosine, tryptophan, and derivatives thereof.

In still another embodiment, the disclosure provides a probe having an electrophilic moiety selected from the group consisting of alkyl halide, haloacetyl, maleimide, aziridine, acryloyl halogen, maleimide, isothiocyanate, isocyanate, acyl azide, N-hydroxysuccinimide ester, sulfonyl chloride, epoxide, oxirane, carbonate, imidoester, carbodiimide, anhydride, diazoalkane, diazoacetyl, carbonydilmidazole, and carbodiimide, and a clickable tag such as alkyne moiety or azide moiety, the clickable tag being optionally covalently linked to a detectable label. In some embodiments, the detectable label can be biotin. Further disclosed herein is the use of the probe compound to perform a biological assay.

DETAILED DESCRIPTION OF THE INVENTION

Figure 1:
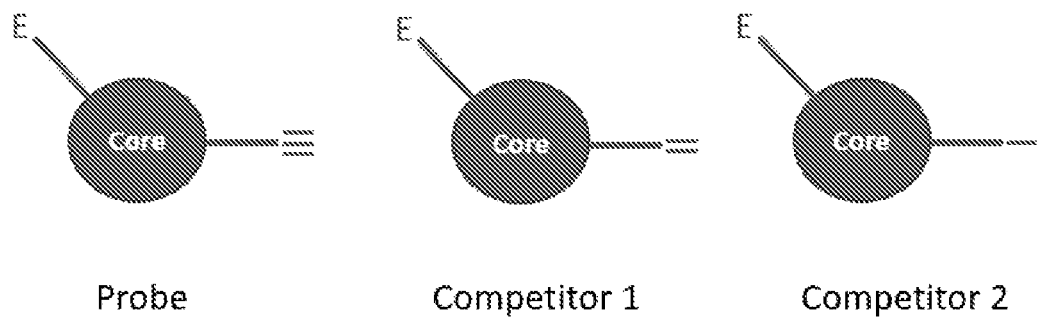
FIG. 1 is a graphical representation depicting probes in one embodiment of the disclosure.

The present invention is based on an innovative method for profiling electrophilic compounds for their covalent interactions with various proteins in complex proteomes. This method can simultaneously identify and quantify the interactions of covalent drugs or covalent drug candidates with thousands of proteins in parallel in whole cell proteomes.

Before the present compositions and methods are described, it is to be understood that this invention is not limited to particular methods and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Electrophilic groups or electrophiles can react with many functional groups, including those present in proteins or polypeptides. In some embodiments, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150, incorporated herein by reference in its entirety. In some embodiments, maleimides can react with amino groups, such as the ε-amino group of the side chain of lysine or 5-guanidino group of arginine, particularly at higher pH ranges. Aryl halides can also react with such amino groups. Haloacetyl derivatives can react with the imidazolyl side chain nitrogens of histidine, the thioether group of the side chain of methionine, the ε-amino group of the side chain of lysine, and the 5-guanidino group of arginine. Many other electrophilic reagents can be used to react with the ε-amino group of the side chain of lysine or 5-guanidino group of arginine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146, incorporated herein by reference in its entirety. Additionally, some electrophilic reagents can react with carboxylate side chains such as those of aspartate and glutamate, such as diazoalkanes and diazoacetyl compounds, carbonydilmidazole, and carbodiimides. These are described in G. T. Hermanson, "Bioconjugate Techniques" (Academic Press, San Diego, 1996), pp. 152-154, incorporated herein by reference in its entirety. Furthermore, electrophilic reagents are known that will react with hydroxyl groups such as those in the side chains of serine, threonine, and tyrosine, including reactive haloalkane derivatives. These are described in G. T. Hermanson, "Bioconjugate Techniques," (Academic Press, San Diego, 1996), pp. 154-158, incorporated herein by reference in its entirety.

In some aspects, electrophile or electrophilic group can include, but is not limited to, alkyl halides, haloacetyl, maleimides, aziridines, acryloyl halogens, maleimides, isothiocyanates, isocyanates, acyl azides, N-hydroxysuccinimide esters, sulfonyl chlorides, epoxides, oxiranes, carbonates, imidoesters, carbodiimides, anhydrides, diazoalkanes, diazoacetyl, carbonydilmidazole, and carbodiimides. In some aspects, the electrophilic group can be selected from the group consisting of

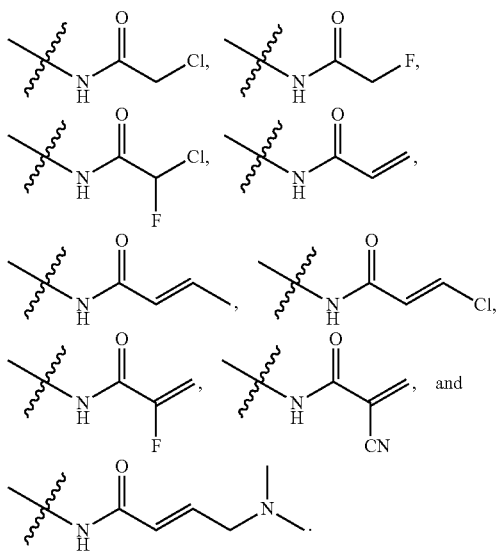

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "alkyl" or "alkane" as used herein, alone or in combination, refers to a straight-chain or branched-chain alkyl group containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl groups include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "acyl" as used herein, alone or in combination, refers to a carbonyl attached to an alkenyl, alkyl, aryl, cycloalkyl, heteroaryl, heterocycle, or any other moiety where the atom attached to the carbonyl is carbon. An "acetyl" group refers to a —$C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "halo", "halide", or "halogen", as used herein, alone or in combination, refers to fluorine, chlorine, bromine, or iodine.

The disclosure provides a method, Isobaric Mass Tagged Affinity Characterization (IMTAC™), for identifying proteins covalently binding to a probe of interest. The method can include: a) contacting a proteomic sample such as live cells or cell lysates or live animals with a probe having an electrophilic moiety and a clickable tag such as an alkyne moiety; and b) analyzing the proteomic sample to detect the proteins that is covalently bound by the probe, thereby identifying the covalent protein targets.

The method can include: a) dividing one proteomic sample into two aliquots; b) contacting a first aliquot with a competitor compound having an electrophilic moiety and lacking a clickable tag; b) contacting the second aliquot from the sample with a DMSO or different amount of the same competitor as that used in a); c) contacting both of the samples with a probe that contains the electrophilic moiety and an additional terminal clickable tag such as an alkyne moiety; and d) identifying the protein target by comparing the amount of probe-bound proteins in two aliquots. In one embodiment, the probe shares the same core structure and the electrophilic moiety as the competitor and contains an additional terminal alkyne moiety. By pre-treating the first aliquot with the competitor compound before reacting the first aliquot with the probe compound, it helps eliminate background interactions between the probe compound and the proteins with nucleophilic amino acid residue, which can serve as a control for the second aliquot, such that only protein targets of interest will be detected.

By identification of a protein target of an electrophilic compound, the protein target will be evaluated for cellular functions and disease relevance. If the protein target plays an important role in the progression of human diseases, e.g. cancer and inflammation, the electrophilic compound may be considered a lead compound, which could be further derivatized and developed as a medicament for treatment of diseases, e.g. cancer or inflammation.

The invention also provides, in various embodiments, proteins identified as targets of an electrophilic compound by the method of the invention.

$$R_1C\equiv CH \qquad \text{Formula (I)}$$

As used herein, an example of the clickable tag is a terminal alkyne moiety includes Formula (I). In some embodiments, $R_1$ can be a Core carrying an electrophilic group, the electrophilic group can be selected from the group consisting of alkyl halides, haloacetyl, maleimides, aziridines, acryloyl halogens, maleimides, isothiocyanates, isocyanates, acyl azides, N-hydroxysuccinimide esters, sulfonyl chlorides, epoxides, oxiranes, carbonates, imidoesters, carbodiimides, anhydrides, diazoalkanes, diazoacetyl, carbonydilmidazole, and carbodiimides.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may include modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, synthetic amino acids and the like), as well as other modifications known in the art.

In some instances, a functional fragment of a polypeptide comprises from about 10 to about 80 amino acid residues in length. In some instances, the functional fragment comprises from about 15 to about 70, from about 20 to about 60, from about 30 to about 50, or from about 40 to about 80 amino acid residues in length. In some cases, the functional fragment comprises about 10, 15, 20, 25, 30, 35, 40, 45, 50, 55, 60, 70, 80, or more amino acid residues in length.

Tandem mass spectrometry (MS/MS or MS$^2$) refers to a technique in instrumental analysis where two or more mass analyzers are coupled together using an additional reaction step to increase their abilities to analyse chemical samples. A tandem mass tag (TMT), belonging to a family of regents referred to as isobaric mass tags, refers to a chemical label used for mass spectrometry (MS)-based quantification and identification of biological macromolecules such as proteins, peptides and nucleic acids.

Scheme 1
Chemical structure of the tandem mass tag (TMT) reagent used in some aspects of the present disclosure.

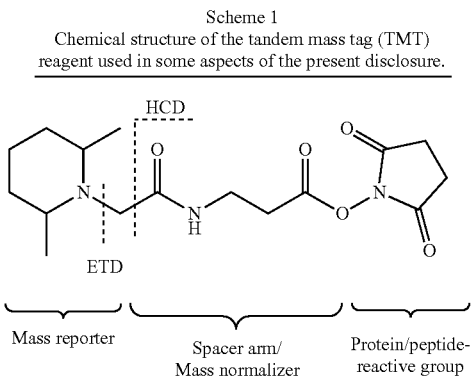

Mass reporter | Spacer arm/ Mass normalizer | Protein/peptide-reactive group

All mass tagging reagents within a set have the same nominal mass (i.e., are isobaric) and chemical structure composed of an amine-reactive NHS ester group, a spacer arm (mass normalizer), and a MS/MS mass reporter, as shown by the chemical structural of an exemplary TMT in Scheme 1. The MS/MS fragmentation sites by higher energy collision dissociation (HCD) and electron transfer dissociation (ETD) are also shown in Scheme 1. The reagents can label peptides prepared from cell-based or tissue samples via the amine-reactive NHS ester group. A unique reporter mass results in the MS/MS spectrum, which are in the low mass region of the MS/MS spectrum. This can be used to report relative protein expression levels during peptide fragmentation from the protein(s) targeted by the probe compound, after enrichment of the target protein via the use of a detectable label.

In some embodiments, the probe compound, after covalently-binding with the target protein, can enable further linking with a detectable label via a clickable tag. A clickable tag is a functionality such as reaction between an alkyne group and an azide group via copper(I) mediated click chemistry. See H. C. Kolb and K. B. Sharpless, *Drug Discovery Today*, 2003, 8(24); 1128-1137, which is incorporated herein by reference.

In some embodiments, a small molecule compound competes with a probe described herein for binding with a reactive amino acid residue. In some instances, a small molecule compound comprises a fragment moiety that facilitates interaction of the compound with a reactive amino acid residue. In some cases, a small molecule compound includes a small molecule fragment that facilitates hydrophobic interaction, hydrogen bonding, or a combination thereof. Often, ligands are non-naturally occurring, or form non-naturally occurring products after reaction with the amino group of a reactive amino acid residue or reactive amino acid residue containing protein.

The following example is provided to further illustrate the advantages and features of the present invention, but it is not intended to limit the scope of the invention. While this example is typical of those that might be used, other procedures, methodologies, or techniques known to those skilled in the art may alternatively be used.

EXAMPLES

Example 1

Proteome-Wide Covalent Ligand Discovery Using Imtac™

A method for profiling electrophilic small molecules for their covalent interactions with various proteins in complex proteomes is described. This method can identify and quantify the covalent interactions between the electrophilic compound and various proteins in the whole cell proteomes, providing new and valuable data that could be further utilized to develop potential therapeutics.

The following methodology was utilized to perform the method of the disclosure.

Divide proteome of living cells or cell lysates into two identical amounts.

Treat the first sample with an electrophilic competitor (Competitor) at a fixed concentration, which can range from 10 nM to 100 µM depending on the reactivity of the electrophile in the Competitor, for 30-240 min.

Treat the second sample with a pure solvent such as DMSO as a negative control. Keep the incubation time consistent as for the first sample (30-240 min).

Treat both samples with an electrophilic probe (Probe) that shares the same core structure and the electrophilic moiety as the Competitor but contains an additional terminal alkyne moiety.

Perform click chemistry reaction with azo-biotin-azide to conjugate a biotin tag to Probe-modified proteins.

Enrich biotinylated proteins with streptavidin magnetic beads.

Perform on-bead tryptic digestion.

Label resulting tryptic peptides with TMT (Tandem Mass Tag), collect and combine labeled peptides in solution.

Cleave the probe-labeled peptides off magnetic beads using sodium dithionite, collect and combine in a separate tube.

Subject the samples from the prior two steps to liquid chromatography-high-resolution mass spectrometry analysis.

The ratio of the intensities of TMT reporter ions for one subject protein between Competitor and DMSO treated samples denote the strength of binding interactions between the Competitor and the subject protein.

The binding affinity ($IC_{50}$) of probe with target proteins can be obtained by varying competitor concentration and using multiplex TMT (6-plex or 10-plex).

FIG. 1 is a schematic showing the probes used in the method while Exhibit A shows illustrative tags that may be utilized, for example to label tryptic digested peptides.

With reference to FIG. 1, "E" on the structural drawing indicates an electrophilic functional group or electrophile; "Core" refers to a core structural of the Probe, Competitor 1, or Competitor 2 molecules; "—" (Competitor 2), "=" (Competitor 1), and "≡" (Probe) indicate the additional functional groups embodied in the individual molecules.

Key aspects of probe design include the following: 1) all reactive probes (referred to herein as the Probe) contain a core structure, an electrophilic group and a clickable tag such as an alkyne tag (alkyne tag will be used as an example for the following description); 2) the corresponding competitor compound (referred to herein as the Competitor) contains the same core structure and electrophilic group but is missing the alkyne tag; and 3) the Probe and the Competitor may have the identical structure to each other with the exception of the alkyne-equivalent moiety (Probe contains a triple-bond-containing terminal alkyne while Competitor 1 and Competitor 2 contain alkene and alkane at the equivalent position instead as shown in FIG. 1).

Example 2

Imtac Screening of SK-MEL-28 Cell Proteome

Preparation of human cancer cell proteomes, SK-MEL-28 cells were cultured in ATCC-formulated Eagle's Minimum Essential Medium (Catalog No. 30-2003) supplemented with 10% fetal bovine serum at 37° C. in a carbon dioxide ($CO_2$) 5% incubator. For in vitro labeling experiments, cells were grown to 90% confluency, washed three times with PBS and scraped in cold PBS. Cell pellets were isolated by centrifugation at 1400×g for 3 min, and the cell pellets stored at −80° C. until further use. The harvested cell pellets were lysed by sonication in PBS buffer. The proteomes were prepared fresh from the frozen cell pellets prior to each experiment.

Scheme 2. Chemical structures of compound 1 and compound 2.

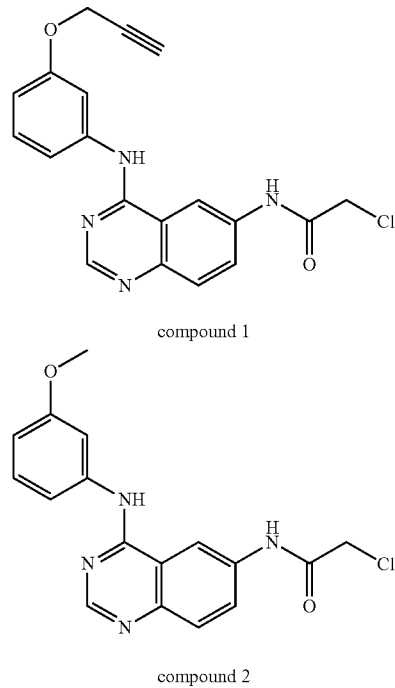

compound 1 compound 2

In vitro compound treatment. Compounds 1 and 2, as shown in Scheme 2, were designed and synthesized according to WO2020/055504 (PCT/US2019/041635), which is incorporated herein by reference. Proteome samples were diluted to a 1 mg protein/mL solution in PBS. For each profiling experiment, one aliquot of the proteome sample (0.5 ml) was treated with 0.5 µl of DMSO as control and the other aliquot was treated with 0.5 µl of compound 2 in DMSO at a final concentration of 0.1 µM. After 60 minutes of treatment at room temperature, ice-cold methanol was added to the samples to precipitate proteins. The precipitates were re-suspended in 0.5 ml of ice-cold DPBS and add 5 µl of 1 tablet of Roche protease inhibitor tablet dissolved in 1 ml of ddH$_2$O.

In situ compound treatment. After SK-MEL-28 cells were grown to 90% confluency in 15 cm petri dishes, incubate Plate 1 with 20 ml of media containing 20 µl of DMSO as a control, and Plate 2 with 20 ml of media containing in 0.1 µM final concentration of compound 2 at 37° C. under 5% $CO_2$ for 30 min to 1 hr. Wash cells with 20 ml of DPBS, incubate both plates with 20 ml of media containing 1 µM of compound 1 for another 30 min to 1 hr at 37° C. under 5% $CO_2$. Harvest cells in 10 ml DPBS using a cell scraper. After spin down with Thermo Sorvall XT centrifuge, resuspend the pellet in 0.5 ml of ice-cold DPBS and add 5 µl of 1 tablet of Roche protease inhibitor tablet dissolved in 1 ml of ddH$_2$O. Cells were lysed using Branson Sonifier probe sonicator, lysate was spin down using Beckman Coulter Microfuge 20R centrifuge, supernatant was collected.

Click chemistry. Each of the mock or compound-treated proteome samples (0.5 mg of cell lysate) was conjugated with Biotin-azo-azide (100 µM final concentration) or DDE-biotin-azide (250 µM final concentration) using click chemistry (acetylene-azide cycloaddition) by adding final concentration of 1 mM TCEP, 25 mM TBTA, and 1 mM $CuSO_4$. Samples were allowed to react at room temperature for 1 hour. After the click chemistry step, ice-cold methanol was added to precipitate proteins.

Enzymatic digestion. Resuspend protein pellet with 200 µl of 1.2% SDS in PBS, Add DTT solution (Final concentration 10 mM) and incubate at 60° C. for 30 min. Incubate with iodoacetamide solution (final concentration of 25 mM for 40 min in the dark at room temperature. Add the samples to the pre-washed magnetic beads and incubate at room temperature for 1 hr with mixing in a tube revolver. Wash beads sequentially with 4 M Urea in PBS and 1.2% SDS in PBS, water, and 100 mM TEAB. Re-suspend beads in 100 µl of 50 mM TEAB and add 4 µl of Lys-C trypsin at 1 mg/ml concentration to each sample. Digest overnight at 37° C. in an Eppendorf Thermomixer.

TMT labeling. TMT labeling was carried out according to manufacturer's instruction. Briefly, immediately before use, equilibrate the TMT Label Reagents to room temperature. For the 0.8 mg vials, add 41 µl of anhydrous acetonitrile to each vial. Allow the reagent to dissolve for 5 minutes with occasional vortexing. Briefly centrifuge the tube to gather the solution. Carefully add 41 µl of each of the TMT Label Reagent to each sample and mix thoroughly by pipetting. Incubate the reaction for 1 hr at room temperature. Add 8 µl of 5% hydroxylamine to the sample and incubate for 15 minutes to quench the reaction. Place the tubes containing samples in the magnetic stand and collect and combine supernatants. Wash each sample with 200 µl of DPBS and combine the wash solutions and repeat once more. Finally, combine supernatants into one tube. Place tube in magnetic stand for several minutes and transfer to new tube to remove residual beads.

LC/MSMS analysis. TMT labeled samples were desalted with Oasis HLB (Waters) solid phase extraction column. After dried down organic eluted samples, reconstitute samples in appropriate 20 µl of 5% ACN, 0.1% formic acid for LC/MSMS analysis. TMT labeled peptides were analyzed using Orbitrap Fusion Lumos Tribrid Mass Spectrometer equipped with Easy-Spray source and Ultimate 3000 Nano-LC system. A PepMap™ RSLC C18 column (2 µm, 100 A, 7.5 µm×25 cm) was used for separation. The mobile phase was consisted of water and acetonitrile using gradient elution. The column was equilibrated and eluted under gradient conditions (Table 1) with a flow rate of 0.3 µl/min. The sample injection volume was 6 µl.

TABLE 1

HPLC gradient elution conditions.

| Time (min) | % B (100% ACN, 0.1% Formic acid) | Flow (µl) |
|---|---|---|
| 0.0 | 2.0 | 0.300 |
| 3.0 | 2.0 | 0.300 |
| 123.0 | 35.0 | 0.300 |
| 124.0 | 90.0 | 0.300 |
| 139.0 | 90.0 | 0.300 |
| 140.0 | 2.0 | 0.300 |
| 155.0 | 2.0 | 0.300 |

Orbitrap Fusion LUMOS Tribrid Mass Spectrometer was operated as follow: full MS resolution was set to 120,000 at m/z 200 and full MS AGC target value was 4E5 with a maximum IT of 50 ms and RF lens value was set to 30. The m/z was set to 375-1575, and the MIPS properties were set to peptide. For MS2 spectra, the intensity threshold was set to 1E4, the ddMS2 IT HCD model was used for MS2 spectra, the isolation width was set to 0.7 m/z, activation type was HCD, HCD collision energy [%] was 38. The AGC target value was set to 1E5, the orbitrap was employed for MS2 detection with 30,000 resolution.

Mass spec data was processed using Proteome Discoverer and an in-house developed software. TMT tag signals were converted into IMTAC score to represent apparent binding affinity between compound 1 and target protein(s). The higher the IMTAC score, the stronger the interaction between compound 1 and the protein.

Figure 2:
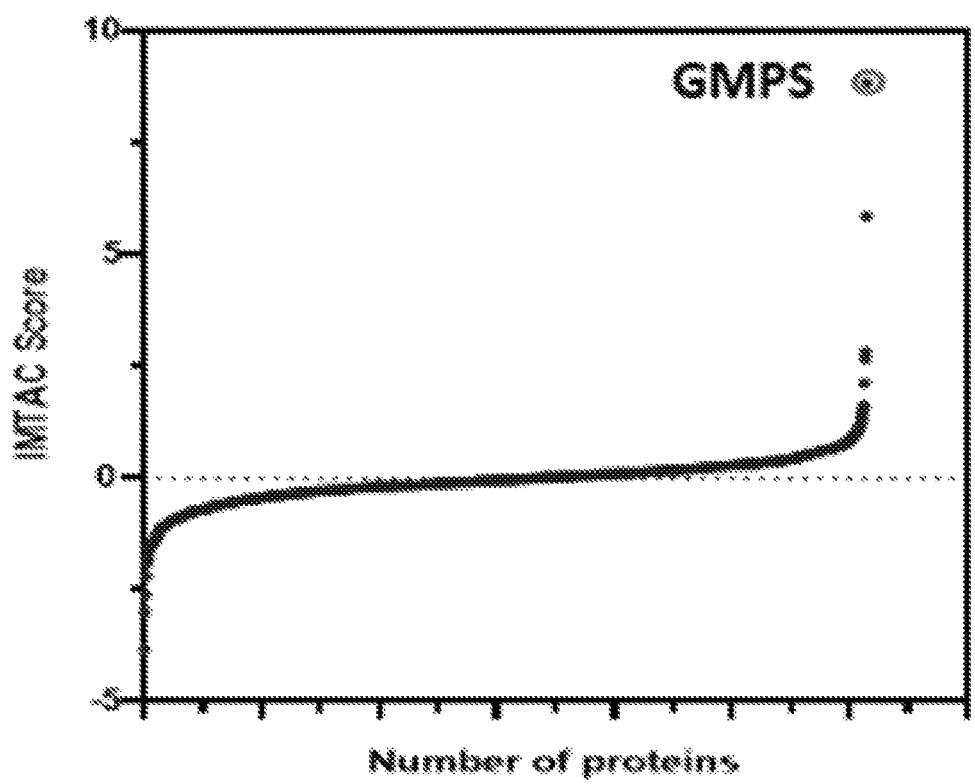
FIG. 2 is a graph showing Guanosine Monophosphate Synthetase (GMPS) identified as the top hit of compound 1 in the proteome in SK-Mel-28 cells, according to some aspects of the present disclosure.

Compound 1 identified hundreds of proteins in IMTAC screening in SK-MEL-28 cells. There is a broad distribution of binding affinity among compound 1 with binding proteins. Guanosine Monophosphate Synthetase (GMPS) was identified as top hit of compound 1, as shown in FIG. 2. FIG. 2 is a graph showing Guanosine Monophosphate Synthetase (GMPS) identified as the top hit of compound 1 in the proteome in SK-Mel-28 cells, according to some aspects of the present disclosure. IMTAC score illustrated in FIG. 2 is derived from the TMC tag signals and essentially provides a relative quantitative value for the binding strength between the tested small molecule and all the different proteins in the sample. An IMTAC score of zero points to almost no binding affinity for the particular protein. A higher IMTAC score indicates a stronger binding strength between the small molecule and the target protein. There is a large IMTAC score difference between top hit GMPS with the $2^{nd}$ hit indicating high selectivity of compound 1 towards GMPS in the proteome.

GMPS is a key enzyme that converts xanthosine monophosphate to guanosine monophosphate. It is a critical component of the de novo purine biosynthetic pathway. Since lymphocyte cells can only use the de novo purine biosynthetic pathway to provide the raw material for DNA synthesis, specifically inhibiting the de novo pathway can prevent the proliferation of immune cells. Therefore, GMPS inhibitor can serve as an immunosuppressive treatment for autoimmune disease, such as SLE (systemic lupus erythematosus).

Compound 1 and GMPS interaction were evaluated using different biochemical and cell-based assays including 1) confirmation of covalent interaction and identification of binding site of compound 1 with GMPS using Mass Spectrometry; 2) measurement of compound 1 and GMPS engagement by in-gel fluorescence; 3) determination of the biochemical $IC_{50}$; and 4) measurement of GMPS activity in the presence of compound 1 using a cell-based assay; 5) efficacy in In vivo study.

Figure 3:
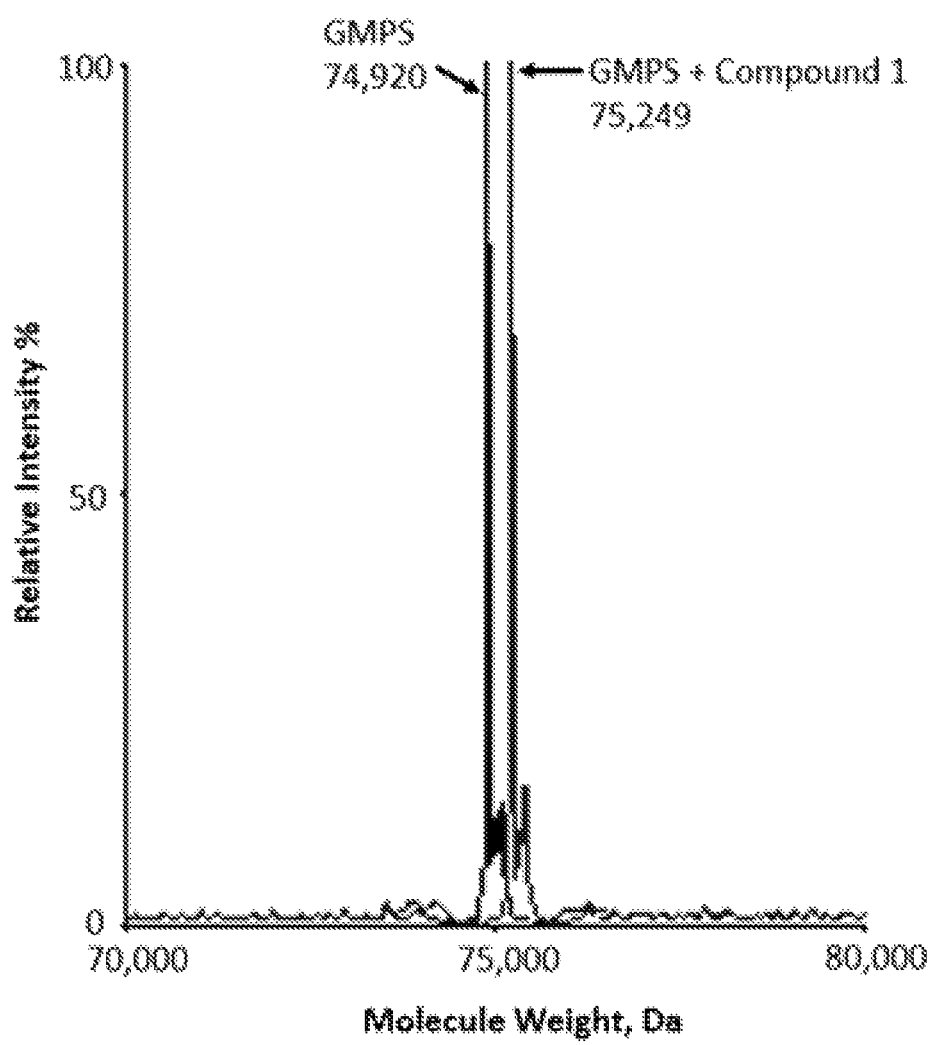
FIG. 3 is a graph showing incubation of recombinant GMPS with compound 1 induced a clean mass shift of 329 Dalton (Da), corresponding to the molecular weight of compound 1.

To confirm covalent interaction of compound 1 with GMPS, recombinant GMPS was incubated with compound 1 in the molar ratio of 1:2 at 37° for 1 hr, a mass increase of 329 Da of the protein was observed using mass spectrometry thus confirming covalent binding, as shown in FIG. 3. FIG. 3 is a graph showing incubation of recombinant GMPS with compound 1 induced a clean mass shift of 329 Dalton (Da), corresponding to the molecular weight of compound 1. The binding site was identified as Cys 104 by analyzing MS/MS of trypsinized GMPS after compound 1 treatment.

Example 3

Characterization of the Binding Between Compound 1 and GMPS

Figure 4:
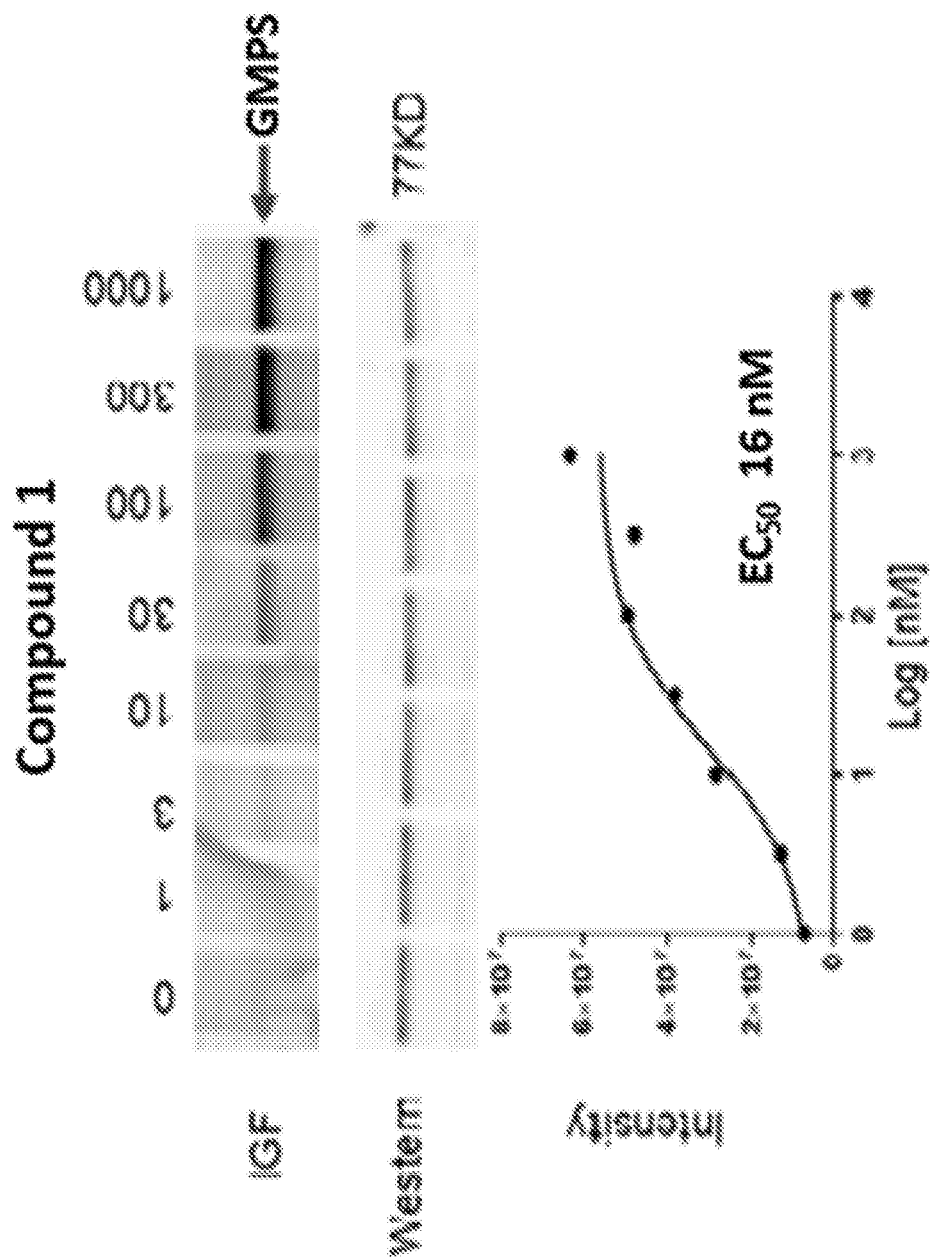
FIG. 4 is a graph showing dose-dependent engagement of GMPS by compound 1 in SK-Mel-28 cells using a fluorescence-based assay.

To measure compound 1's target engagement to GMPS, HEK293 cells were grown to ~90% confluence in 6-well plates with proper media containing 10% FBS. The growth media was removed, and the cells were treated with fresh media containing various concentrations of probe (1,000× stock solution in DMSO) or vehicle control for the 30 min. For the $IC_{50}$ measurements, cells were first incubated with compound 2 at 1 nM to 1000 nM with 3× interval for 30 min at 37° C. and then treated with 100 nM compound 1 for another 20 min at 37° C. After the probe treatment, the media was removed, and the cells were washed twice with ice-cold Dulbecco's PBS (DPBS). The cells were harvested, and the pellet was re-suspended in 80 µL of NP40 lysis buffer (50 mM HEPES, pH 7.4, 1% NP-40, 150 mM NaCl) with protease inhibitor cocktail (Roche). The lysate was incubated on ice for 20 min and fractionated by centrifugation at 18,000×g for 10 min at 4° C. The protein concentrations were measured from each of the supernatant samples by BCA assay (Pierce) and adjusted to 1 mg/ml. CuACC was performed at a final concentration of 25 µM TAMRA-azide (Click Chemistry Tools), 1 mM Tris(2-carboxyethyl)phosphine (TCEP, Thermo-Scientific), 100 µM Tris[(1-benzyl-1H-1,2,3-triazol-4-yl)methyl]amine (TBTA, TCI), and 1 mM CuSO4 (Sigma-Aldrich) in a total volume of 100 µl. The reaction was performed at RT for 1 h in the dark before termination by addition of 40 µl of 4× Laemmli sample buffer (Bio-Rad) and boiled for 5 min. 30 µl of the samples were loaded and resolved on a 4-20% SDS-PAGE before visualization at 532 nm for excitation and 610 nm for emission on a ChemiDoc MP Imaging System (Bio-Rad). Fluorescence images were displayed as gray scale and the intensities of the fluorescent signals were quantified using ChemiDoc quantification software, as shown in FIG. 4. FIG. 4 is a graph showing dose-dependent engagement of GMPS by compound 1 in SK-Mel-28 cells using a fluorescence-based assay. The $EC_{50}$ (16 nM) value was calculated with GraphPad Prism software (GraphPad Software, La Jolla, CA.)

Figure 5:
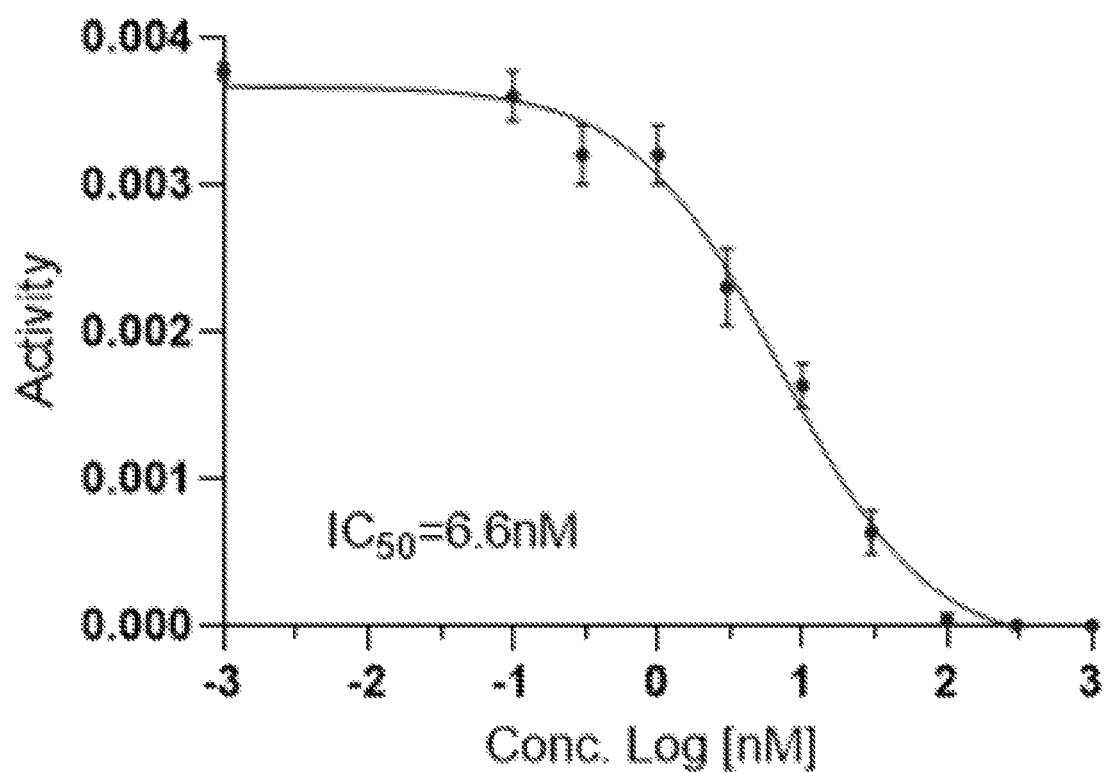
FIG. 5 is a graph showing determination of $IC_{50}$ for compound 1 using a spectroscopic assay by monitoring the decrease of absorbance at 290 nm.

For biochemical $IC_{50}$ determination, the reaction buffer was prepared containing EPPS (pH 7.8), EDTA (100 µM), $MgCl_2$ (10 mM), ATP (2 mM), XMP (200 µM), Glutamine (5 mM). The blank buffer was prepared with the same ingredients at equal concentrations except for the absence of XMP. Protein solutions were prepared in EPPS (pH 7.8) at varying concentrations (ranging from 0.1 μM to 100 μM). UV-vis was set to kinetics mode and the absorbance wavelength was set to 290 nM. Following auto zeroing with the blank buffer, 495 μl of the reaction buffer was incubated with 5 μl of each protein solution, 0.5 μL of 1000× of the desired concentration of the drug was added to the reaction mixture, and the decrease of absorbance at 290 nM over 30 min was observed. $IC_{50}$ values for probes and competitor molecules were calculated using the non-linear regression "Dose Response-Inhibition" model on Prism 7 software (GraphPad Software, La Jolla, CA). compound 1 was shown to be very potent with an $IC_{50}$ of 6.6 nM, as illustrated in FIG. 5. FIG. 5 is a graph showing determination of $IC_{50}$ for compound 1 using a spectroscopic assay by monitoring the decrease of absorbance at 290 nm.

Example 4

In Vivo Characterization of the Therapeutic Effect of Compound 1

Figure 6:
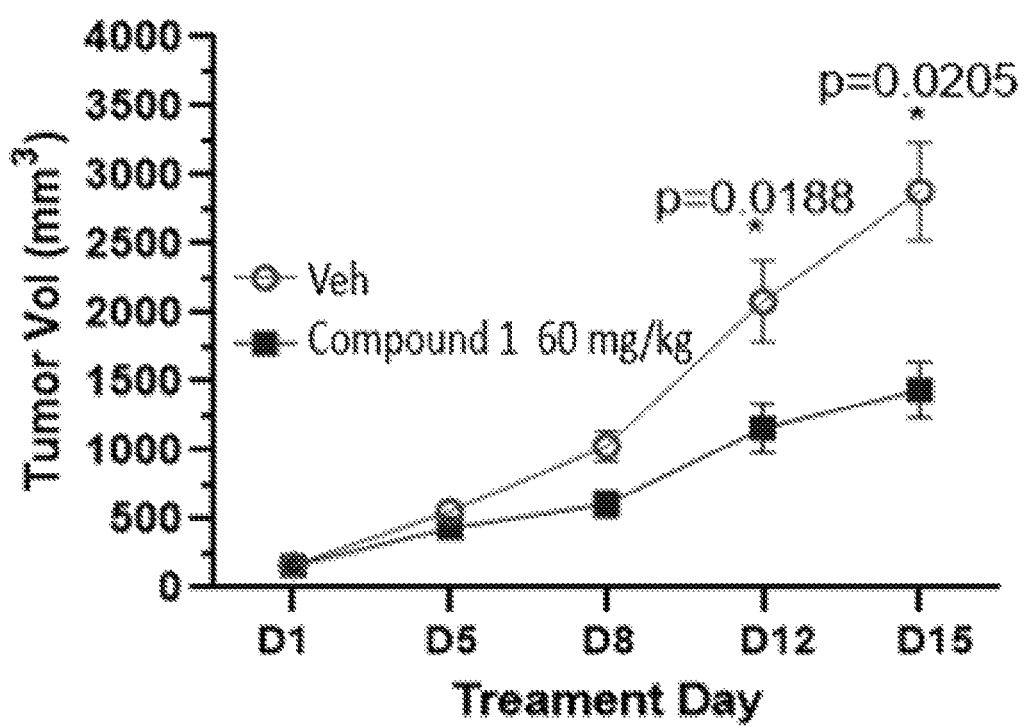
FIG. 6 is a graph illustrating compound 1 inhibition of SK-ML-28 tumor growth.
Figure 7:
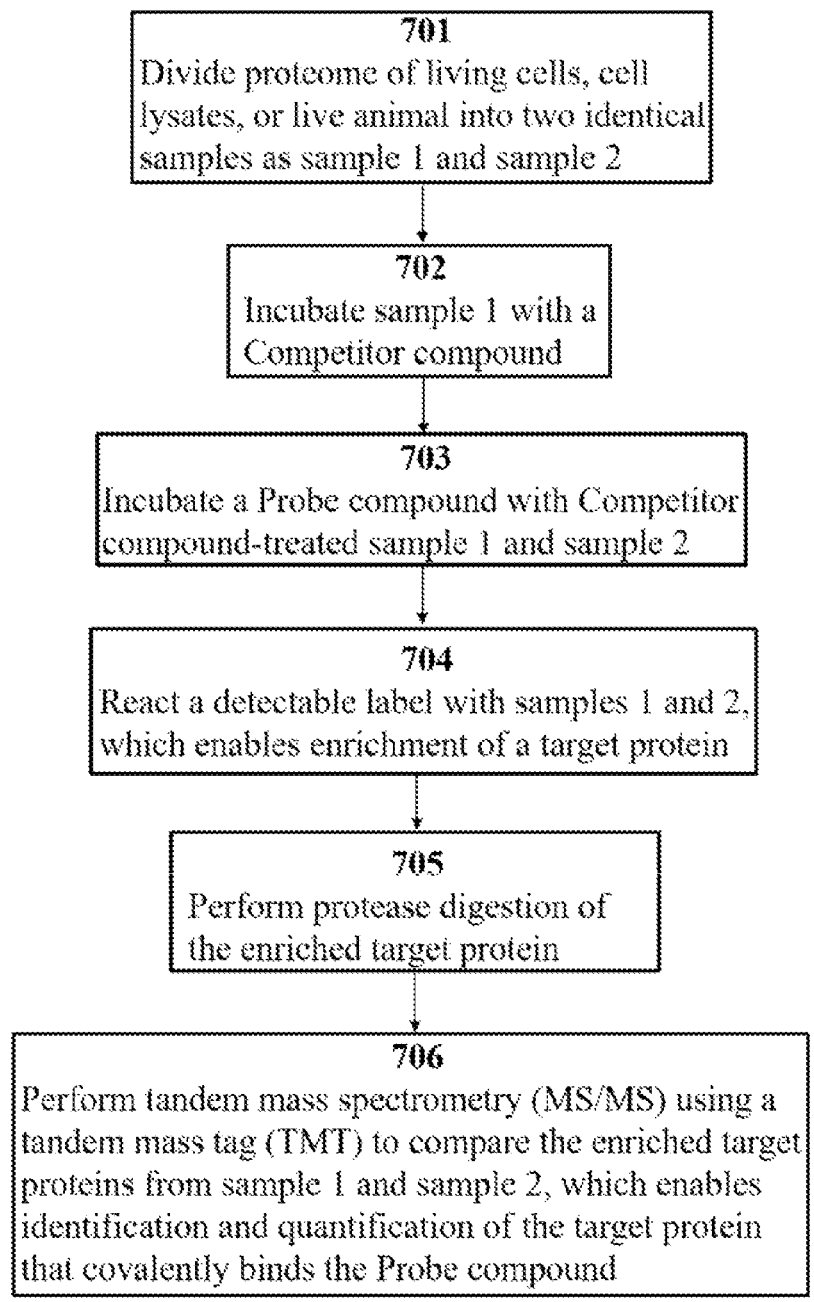
FIG. 7 is a flowchart illustrating a method of identifying a protein target, according to some aspects of the present disclosure.

A melanoma CDX model was used to provide in vivo confirmation of the therapeutic potential of compound 1 through targeting the de novo purine salvage pathway. For this model, BALB/c nude mice were inoculated subcutaneously (sc) with SK-MEL-28 tumor cells ($5 \times 10^6$ in 0.1 mL PBS and Matigel, 1:1). Once tumor size reached approximately 150 mm³ (100-250 mm³), compound 1 treatments were initiated and were given subcutaneously twice a day for 5 days followed by once a day for 9 days. Throughout the treatment period, tumor sizes were recorded. Compound 1 was able to reduce tumor size compared to control starting at day 8 with the difference in reduction increasing through the end of the treatment period, as shown in FIG. 7. Compound 1 inhibited SK-ML-28 tumor growth. 60 mg/kg of compound 1 was given subcutaneously twice a day for 5 days followed by once a day for 9 days. Vehicle control consisted of 5% DMSO and 95% of a 20% 2-hydroxypropyl-beta-cyclodextrin solution. Eight female mice were included in each group. t-test was done using GraphPad Software. FIG. 6 is a graph illustrating compound 1 inhibition of SK-ML-28 tumor growth. The overall trend shown in FIG. 6 provided evidence that the in vitro activities translated to an in vivo environment and indicated that the potency of compound 1 needs to be enhanced to achieve a statistically significant demonstration of in vivo efficacy.

FIG. 7 is a flowchart illustrating a method of identifying a protein target, according to some aspects of the present disclosure. Step 701 divides proteome of living cells, cell lysates, or live animals into two identical samples as sample 1 and sample 2. Step 702 incubates sample 1 with a Competitor compound. Step 703 incubates a Probe compound with Competitor compound-treated sample 1 and sample 2. Step 704 reacts a detectable label with sample 1 and sample 2, respectively, which enables enrichment of a target protein. Step 705 performs protease digestion of the enriched target protein. And step 706 performs tandem mass spectrometry (MS/MS) using a tandem mass tag (TMT) to compare the enriched target proteins from sample 1 and sample 2, which enables identification and quantification of the target protein that covalently binds the Probe compound.

Although the invention has been described with reference to the above examples, it will be understood that modifications and variations are encompassed within the spirit and scope of the invention. An illustrative example of the invention is attached herein as Exhibit A which is herein incorporated by reference in its entirety. Accordingly, the invention is limited only by the following claims.

What is claimed is:

1. A method for identifying a protein target comprising:
   a) contacting a first protein-containing sample comprising a protein target with a competitor compound comprising a core structure and an electrophilic moiety to obtain a sample treated with the competitor compound, wherein the electrophilic moiety binds a nucleophilic amino acid residue in the protein target; the competitor compound does not comprise a terminal clickable tag; and the first protein-containing sample is selected from the group consisting of live cells, cell lysates, and live animals;
   b) contacting the sample treated with the competitor compound of step a) with a probe compound comprising (i) a core structure and an electrophilic moiety that are identical to the core structure and the electrophilic moiety of the competitor compound, and (ii) a terminal clickable tag, wherein the clickable tag is a terminal alkyne moiety;
   c) contacting a second protein-containing sample comprising the protein target with the probe compound, wherein the second protein-containing sample has not been contacted with the competitor compound; and
   d) identifying the protein target by detecting the probe compound-modified proteins in the first protein-containing sample as compared to those in the second protein-containing sample.

2. The method of claim 1, wherein the probe compound-modified proteins are further derivatized with a detectable label via the clickable tag.

3. The method of claim 2, wherein the detectable label comprises biotin.

4. The method of claim 3, wherein the nucleophilic amino acid residue in the protein target is selected from the group consisting of arginine, lysine, histidine, cysteine, methionine, aspartic acid, glutamic acid, serine, threonine, tyrosine, and tryptophan.

5. The method of claim 3, wherein the electrophilic moiety is selected from the group consisting of alkyl halide, haloacetyl, maleimide, aziridine, acryloyl halogen, isothiocyanate, isocyanate, acyl azide, N-hydroxysuccinimide ester, sulfonyl chloride, epoxide, oxirane, carbonate, imidoester, anhydride, diazoalkane, diazoacetyl, carbonyldimidazole, and carbodiimide.

6. The method of claim 1, wherein the electrophilic moiety is selected from the group consisting of

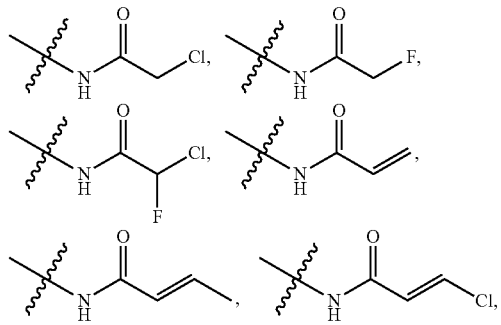

-continued

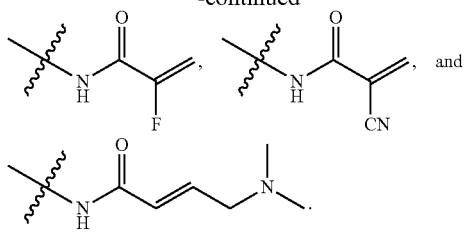

7. The method of claim 1, further comprising respectively reacting the first protein-containing sample and the second protein-containing sample with a compound comprising a detectable label and a group reactive with the clickable tag in the probe compound, thereby forming a detectable label-tagged protein target.

8. The method of claim 7, further comprising enriching the detectable label-tagged protein target.

9. The method of claim 8, further comprising preforming protease digestion of the enriched protein target.

10. The method of claim 1, wherein step d) further comprises quantifying binding interactions between the competitor compound and the protein target and/or wherein step d) is performed using LC-MS/MS with a tandem mass tag (TMT).

11. The method of claim 10, wherein, prior to step a), the method further comprises dividing a proteome into two equivalent protein-containing samples, thereby obtaining the first protein-containing sample and the second protein containing sample.

* * * * *

UNITED STATES PATENT AND TRADEMARK OFFICE
CERTIFICATE OF CORRECTION

| | | |
|---|---|---|
| PATENT NO. | : 12,392,778 B2 | Page 1 of 1 |
| APPLICATION NO. | : 17/630815 | |
| DATED | : August 19, 2025 | |
| INVENTOR(S) | : Ping Cao et al. | |

It is certified that error appears in the above-identified patent and that said Letters Patent is hereby corrected as shown below:

In the Claims

Column 14, Claim 4, Line 37, replace "The method of claim 3" with --The method of claim 1--;

Column 14, Claim 5, Line 42, replace "The method of claim 3" with --The method of claim 1--.

Signed and Sealed this
Tenth Day of February, 2026

John A. Squires
*Director of the United States Patent and Trademark Office*